United States Patent [19]
Tischlinger

[11] 3,987,940
[45] Oct. 26, 1976

[54] GLASS TUBE AND THERMOPLASTIC RESIN FINGER-GRIP AND NOSE SLEEVE SYRINGE BODY ASSEMBLY

[75] Inventor: Edward A. Tischlinger, Des Plaines, Ill.

[73] Assignee: MPL, Inc., Chicago, Ill.

[22] Filed: Mar. 18, 1974

[21] Appl. No.: 451,925

Related U.S. Application Data

[62] Division of Ser. No. 197,718, Nov. 11, 1971, abandoned.

[52] U.S. Cl. .............................. 222/386; 128/218 R
[51] Int. Cl.² .......................................... A61M 5/28
[58] Field of Search .................. 222/386, 386.5, 41, 222/44; 128/218 P, 218 R, 218 PA, 218 N, 218 NV, 218 M, 218 G, 218 S, 218 C, 218 D, 218 DA

[56] References Cited
UNITED STATES PATENTS

| | | |
|---|---|---|
| 2,887,108 | 5/1959 | Mendall .......................... 128/218 N |
| 3,366,286 | 1/1968 | Mloehn .............................. 222/386 |
| 3,417,904 | 12/1968 | McLay ........................ 128/218 C X |
| 3,470,604 | 10/1969 | Zenich ................................ 264/249 |

*Primary Examiner*—Robert B. Reeves
*Assistant Examiner*—Frederick R. Handren
*Attorney, Agent, or Firm*—Kinzer, Plyer, Dorn & McEachran

[57] ABSTRACT

A glass tube and thermoplastic resin finger-grip and nose-forming sleeve syringe body assembly in which, the finger-grip sleeve and the nose-forming sleeve are each cam-stretched onto and frictionally retained on respective opposite ends of a glass tube, which is a section of die-formed glass tubing. Increase in latitude of operable interference fit and stretch is effected by assembling the finger-grip and nose-forming sleeves onto the glass tube while the sleeves are in a heated condition.

2 Claims, 8 Drawing Figures

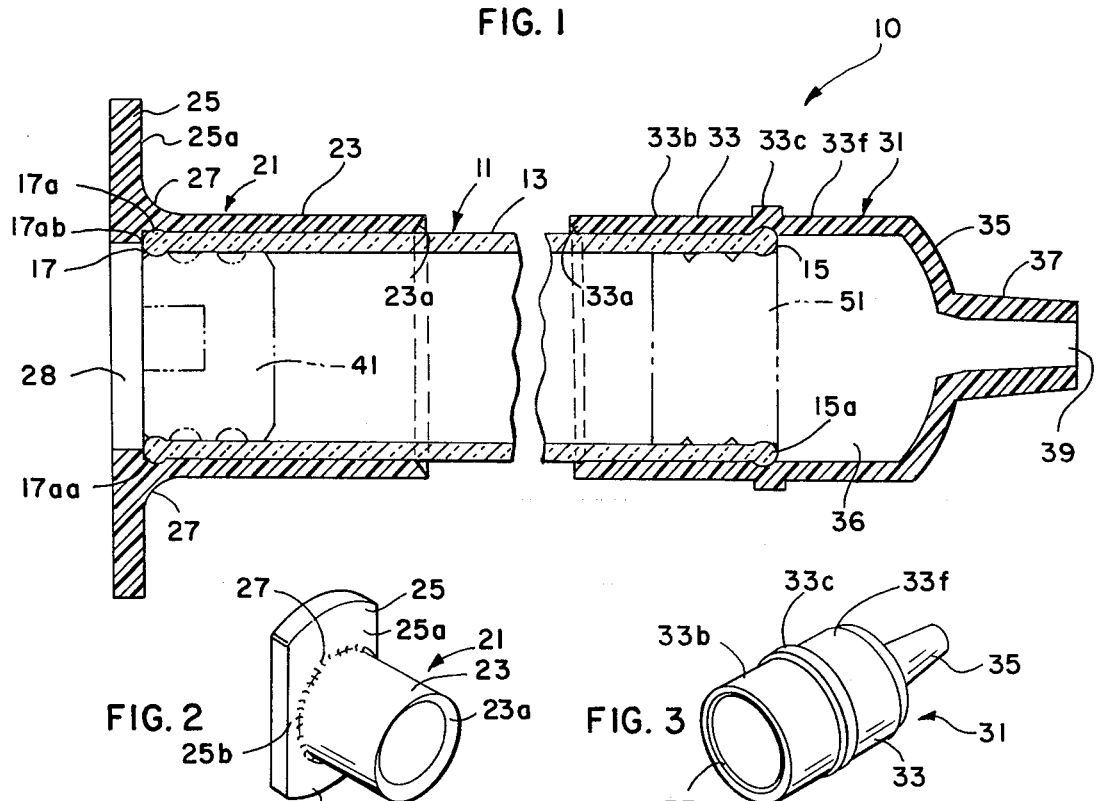
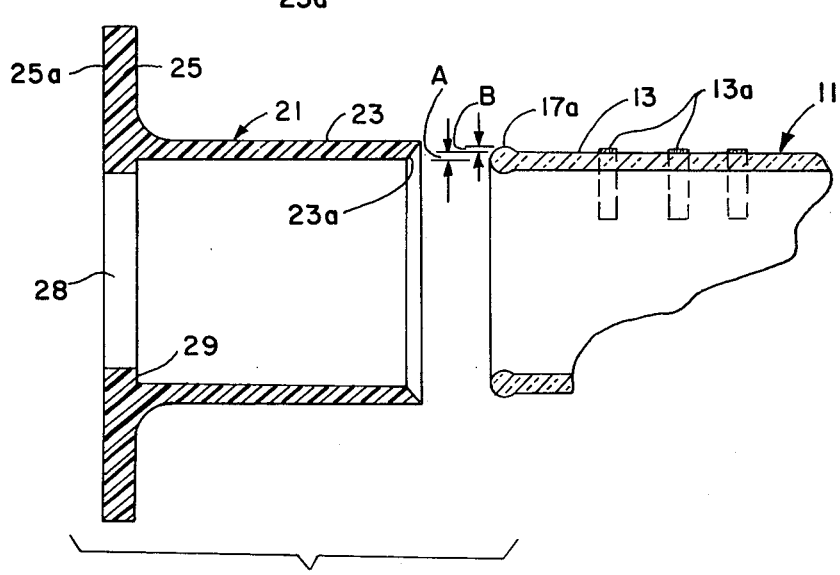

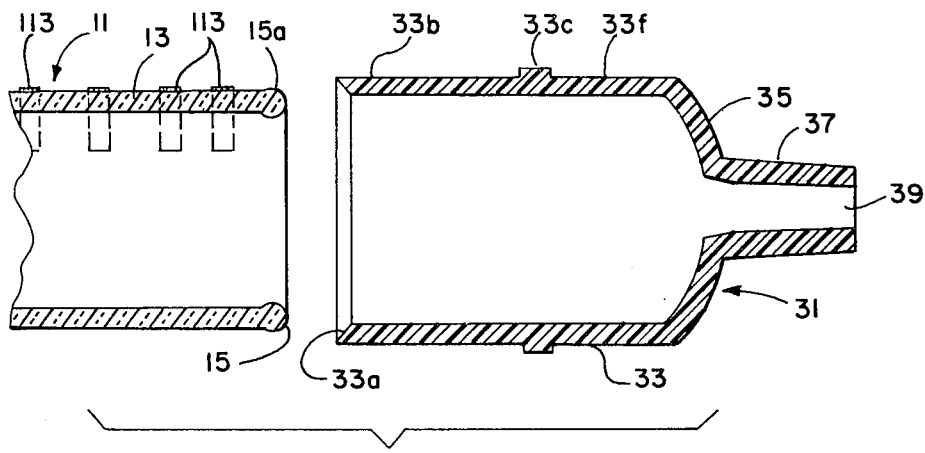
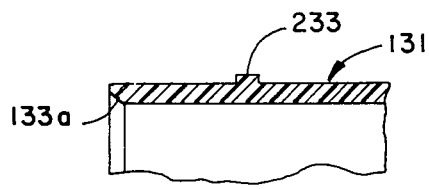 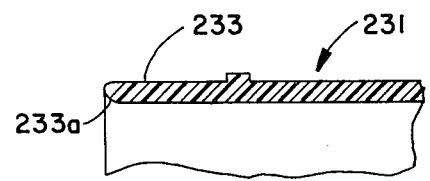
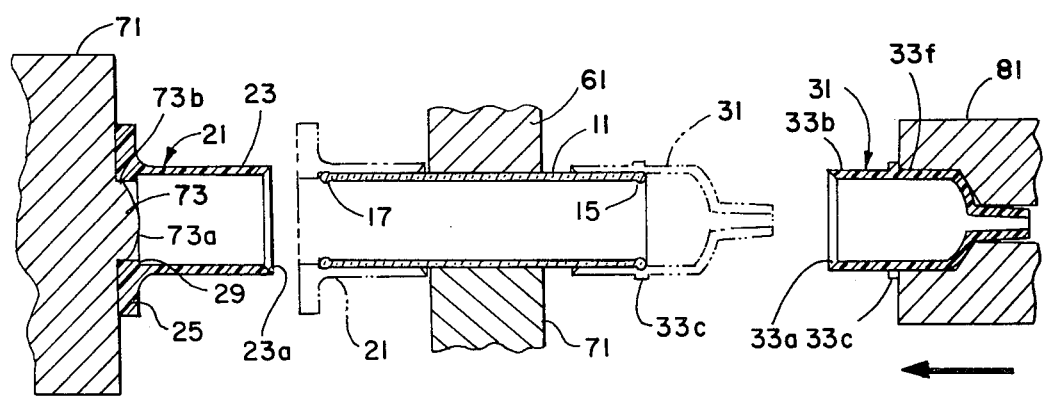

GLASS TUBE AND THERMOPLASTIC RESIN FINGER-GRIP AND NOSE SLEEVE SYRINGE BODY ASSEMBLY

This is a division of application Ser. No. 197,718, filed Nov. 11, 1971, now abandoned.

This invention relates to a syringe body assembly for use in prefilled packaging and long-term containment and subsequent dispensing, of liquid drugs and other pharmaceutical chemicals, and relates more particularly to a syringe body having a glass tube liquid containment mid-section, with theromplastic resin finger grip sleeve and nose-forming sleeve on the opposite tube ends, a successful thermoplastic resin having been found to be polypropylene.

It has been common in the syringe art to provide syringes formed from both glass and plastic materials. It is known that glass syringes have an important advantage of providing a clear and chemically inert container for drugs and other chemicals which are desired to be injected. The transparency of the glass enables the ready detection of any visible foreign particulate matter, and in addition the relatively chemically inert characteristic of syringe glass materials enables the injectable drug or chemical to be left in contact with the glass walls of the container for substantial periods of time without altering the chemical properties of the drug by combination with chemicals in the syringe material or by evaporation through the container wall of various chemical constituents in the drug or other chemical liquid. Thus, it is a particular advantage to be able to employ the advantageous properties of glass when packaging and storing drugs over a long period of time. Typically, a type of glass known as Type I or boro-silicate glass, is used for this purpose, having a high order of ehcmical inertness. However, this type of glass is somewhat difficult to handle in manufacturing a syringe by forming operations on a glass tube, and as a syringe formed with its entire body of glass requires the opposite ends of the glass body to be formed to provide finger-grip flanges at one end and a nose tip at the opposite end or to adhere suitable finger grip and nose-forming glass end pieces thereto, for dispensing and attachment to further units such as hypodermic needles, or for use simply for dispensing it will be readily appreciated that such all-glass syringe bodies are troublesome and expensive to manufacture, and have other substantial drawbacks, including that of ease and danger of breakage of the end formed or secured sections, as in so forming or securing, stresses are set up in the glass, and weak spots are developed which cause the syringe to be subject to breakage at these points. This is a particularly important hazard for the finger-grip flange section, as breakage at this point may cause cutting of an operator and/or the patient. In addition, the breakage may take place in the course of handling the syringe body after formation of the flange and nose tip ends thereon, as in the course of filling the syringe, inserting a plunger piston therein, printing of the syringe body, etc. However a special hazard is the possibility of the flange breaking during use, as all-glass syringes have been known to cause serious finger cuts due to breakage of the flange when pressure is applied during the actual injection procedure. Thus, there are two major disadvantages in the use of all-glass syringes, namely the high cost of providing the flange and nose tip end, and the hazard of breakage.

These two disadvantages of cost and breakage hazards are readily overcome by the use of plastic syringes, and particularly injection-molded plastic syringes and syringe body components; however, all-plastic syringes have been found generally unsuitable for storage of drugs and other active chemicals, and therefore are unusable for a prefilled syringe. The chemical makeup of substantially all thermoplastic and thermosetting resins is such that there is an appreciable chance of the contained drug combining with chemicals in the plastic, or in other instances the plastic may act in an absorptive fashion, having a tendency to absorb the chemicals out of the drug into the plastic, thus changing the chemical constituency and for relative proportions of the drug or other chemical liquid contained in the plastic syringe body. In addition, it is also well known that all thermoplastic resins have a moisture vapor transmission characteristic which can cause an undesired loss of fluid during long periods of storage.

In a third type of prior art syringe arrangements related to this problem, a tubular glass element has been attempted to be used with thermoplastic resin parts assembled to the glass. In such known arrangements, the thermoplastic resin parts have been secured to the glass by the use of adhesives. However, adhesive securing is slow, messy, and provides an undesirable opportunity for the adhesive material to subsequently come into contact with the contained drug or other liquid chemical, which would of course endanger the chemical purity of the drug. In addition, while it might be possible to form a plastic member onto a glass tube through an insert mold process, such insert mold process requires very close tolerance controls, which would not normally be available when employing commercially available glass tubing, which is supplied with a fairly wide tolerance variation. Screw-on mechanical connections between a glass tube and a plastic member are generally less than wholly advantageous, as the formation of such threads on the glass tube create an expense, and in addition create stress conditions which may cause breakage, as well as require a close tolerance control to effect an effective seal in those instances where sealing may be required. While snap-over lip-type plastic cover caps have been employed in various fashions to fit over a beaded glass mouth, such as a bottle mouth, such snap-over cover cap lip connection arrangements are not at all satisfactory for syringe construction, as the interference snap fit interconnection formed thereby is short and does not provide sufficient retentive resistance to pull-off forces to enable its satisfactory use for glass tube and plastic finger grip or nose piece connections in syringe use assemblies. Minimal reliable pull-off force resistance of the order of approximately 5-8 pounds and more is often necessary, and higher orders of resistance are desirable for insured reliability.

It is accordingly a feature of the present invention to overcome the disadvantages of the prior art described above, by utilizing the advantages of a glass tube as a drug or other chemical storage container, while utilizing the inexpensive and reliable mechanical properties of an injectable thermoplastic resin for the finger-grip sections and nose-forming at the opposite ends of a syringe body assembly having a glass tube central body section which may be readily employed as a filling container and as a subcombination constituent portion of a syringe. This assembly is particularly advantageous, enabling ease of mechanical handling of the glass tube, both before and after assembly with the plastic finger grip and nose-forming sections, during the various manufacturing operations performed thereon, including washing, feeding, sterilizing and printing of graduations or legends onto the glass tube, without the substantial disadvantages afforded in such handling and processing operations which are encountered when the tube has a glass flange formed thereon. In addition, it will be appreciated that by employment of the glass tube as the main body section in the subsequent forming of the syringe body assembly, the open-ended glass tube may be prefilled and sealed at its opposite ends prior to or after assembly, with the two plastic end sleeves forming the finger grip and nose-forming sleeves, thus affording material and important assembly and handling advantages, and the glass tube section further may thereby contain a desired drug or other chemical liquid without necessity for the liquid to come into contact with the plastic flange during an extended storage period. In such arrangement, the opposite ends of the glass tube may be suitably sealed off after filling and prior to or after assembly of the plastic end sleeves thereon, and will enable the glass tube with its prefilled liquid contents to thus remain sealed during an extended storage period. The seals are not a part of the present invention, it being appreciated that various constructions and arrangements may be utilized within the scope and intent of the present invention.

In effecting my invention, various thermoplastic resins have been attempted to be employed and great difficulty has been encountered in attempting to resolve this problem, as the various thermoplastic resins have been found to exhibit various difficulties, including either cracking or rupturing of the finger grip and nose-forming sleeves or breakage of the glass, insufficient retention resistance, inadequate elasticity with sufficient retention capability, too much flexibility, and long- and short-term creep, with resultant long- and short-term cracking and/or loosening. However, by careful selection of parameter limits for the glass tube and thermoplastic finger grip in practicing the present invention, I have been able to successfully form a glass tube and thermoplastic resin finger grip assembly which may be simply and reliably manufactured and utilized. The particular thermoplastic resin material which I have found usable in practicing this invention is polypropylene.

The present invention is therefore directed to a syringe body assembly having a glass liquid containment body tube and thermoplastic resin finger grip and nose-forming opposite end, the details of which are described in the course of the following description of the invention.

Still other objects, features and attendant advantages will become apparent to those skilled in the art from a reading of the following detailed description, taken in conjunction with the accompanying drawings wherein:

FIG. 1 is a longitudinal section view of a syringe body constructed in accordance with the invention.

FIGS. 2 and 3 are perspective views of the finger grip sleeve and nose-forming sleeve of the embodiment of FIG. 1.

FIG. 4 is a fragmentary exploded view in longitudinal section of a finger grip sleeve and the adjacent open end of a glass tube, prior to assembly.

FIG. 5 is a view similar to FIG. 4, of a nose-forming sleeve and adjacent glass tube end prior to assembly.

FIGS. 6 and 7 are fragmentary longitudinal section views of modifications of sleeve entrance ends as applied in a nose-forming sleeve.

FIG. 8 illustrates a method of assembly of the arrangement of FIG. 1.

Referring now in detail to the figures of the drawing, a syringe body assembly 10 includes a straight cylindrical glass tube 11 with thermoplastic resin finger grip sleeve 21 and nose-forming sleeve 31 secured onto and over a substantial wall length of its opposite ends 17 and 15 respectively. The glass tube 11 may be suitably formed of a length of straight cylindrical tubing which may be conventionally formed by a die-formed melt process, and subsequent cutting into sections to form desired lengths of glass tubing to be utilized for the glass tube 11. Glass tube 11 includes a straight cylindrical tubular wall 13, which is preferably fire-polished at its opposite ends 15 and 17 to form a fire-polished bead thereon. As an alternative, the opposite ends may be lightly or heavily beveled at their outer annular edge as by grinding or sanding. The fire-polished beads 15a and 17a, at the respective tube ends 15 and 17, may be conventionally formed, and preferably are relatively small, adding on the order of 0.001–0.005 inch diameter to the external diameter of the glass tube, although greater bead size formations may be utilized for given end uses, particularly where internal diameter restrictions are not critical or of material importance. Likewise, while the fire-polished bead 17a is of some material advantage in enhancing the retentive capability of the finger grip 21 on the glass tube 11, fire-polishing without formation of a noticeable bead may be effected, as by employing a forming mandrel, to an acceptable extent of end sleeve assembly capability.

The finger grip sleeve 21 is formed with a finger grip section 25 and a tubular sheath 23 which frictionally engages with the outer longitudinal surface of the glass tube 11 adjoining end 17, and nose-forming sleeve 31 has a dispenser/connector tip section 37 integrally connected through an end wall 35 to a tubular sheath section 33, which frictionally engages with the adjoining longitudinal outer surface of the glass tube 11 adjoining end 15 thereof. Both sleeves are frictionally cam-stretched into interference fit over and along the respective contiguous end wall surfaces of glass tube 11, and as the applicable parameter considerations for both sheaths 23 and 33 relative to glass tube 11 are generally the same, the parameter considerations will first be discussed with respect to the finger grip sleeve 21, and various differences applicable to nose-forming sleeve 31 will then be considered and discussed.

As is seen in FIG. 4, the tubular sheath section 23 of the finger grip sleeve 21 has an inner wall surface c which has a lesser radius than the outer radius of tubular wall 13 of glass tube 11, by an interference amount indicated by the reference character A, the increase in radius of the glass tube by the bead 17a being indicated by the reference character B. Thus, the increase in diameter afforded by the bead 17a is 2B, and the diameter interference between the exterior diameter of the tube wall 13 and the tubular sheath inner wall surface is 2A, according to the reference characters of this Figure. This interference value 2A is of substantial criticality in affording successful operation in accordance with the invention, particularly in light of the conventional practice of supplying glass tubing with a fairly wide tolerance range of diameters from a nominal specified diameter, as practical utilization of the invention requires that the tubing either be utilized as directly supplied from the manufacturer or by internal sorting at some point prior to assembly use, to reduce the tolerance limits to an acceptable range. It has been found that the present invention may be practiced within the tolerance limits of glass tubing as such is conventionally supplied, according to one preferred inventive aspect and mode of practice, and according to a broader but substantially less desirable aspect and mode of practice by sorting the glass tubing and reducing the tolerance levels between the glass tubes of a given lot to an acceptable level for utilization according to this less desirable modified form of practicing the invention. Thus, the preferred mode of practice of the invention in which the thermoplastic resin is preheated and is in a heated state during assembly, as will be later described, may be practiced as applied to standard die-formed glass tubing and thermoplastic resin in the form of polypropylene, with glass tube tolerance levels of the order of approximately 0.034–0.035 inch diameter variations of standard commercially supplied glass tubing of approximately 0.4 inch outer diameter as supplied in readily available commercial lots, and the modified and less desirable aspect of the invention may be practiced through the aid of sorting with tolerance levels for this diameter of glass tubing reduced to approximately 0.025–0.027 inch.

In addition, the bead 17a may be, for a given tolerance range, of greater consequency in the modified form of practice of the invention and may be preferably held to a minimum, as of the order of 0.001–0.002 inch, or less, raised diameter increase for this and other practical considerations of use.

One or both of the end 17 of tube 11 and the facing end 23a of sheath 23 is formed with a cam surface which exerts a radially and circumferentially stretching action on the sheath 23 as a function of pressing of the sheath 23 axially against and onto the open end 17 of glass tube 11. As the glass tube 11 itself is essentially rigid as compared to the thermoplastic resin sheeve 21, the camming action will result in the tube sheath 23 stretching in diameter and circumference and forming an elastically enlarged contiguous binding ring of substantial longitudinal extend about and along the longitudinal annular surface of tube 11 upon the complete pressing of the tubular sheath 23 of finger grip sleeve 21 onto the glass tube 11. This also sets up internal stresses in both the sleeve sheath 23 and the glass tube 11, which must be accommodated in practicing the invention.

This interference stretch-fit press-on of the finger grip sleeve 21 is preferably terminated by a annular shoulder 29 forming a radially inward extension of the rear finger grip flange section of the finger grip sleeve 21. One preferred form of the shoulder 29 is illustrated, in which the shoulder 19 forms a thru-bore 28 which is of at least as great a diameter as the effective internal diameter of the tube 11. This enables the subsequent ready insertion and removal of a conventional or other elastic plunger position, schematically indicated in phantom outline at 41, as may be desired for ultimate use of this assembly, and also enables a manually operable plunger to be connected and operated there through by external manual manipulation. Alternatively, the shoulder 29 may extend radially inwardly to form a thru-bore 28 which may be of lesser diameter than the effective internal diameter of the glass tube 11, thereby affording a shoulder stop which will impede the removal of a plunger piston 41 after insertion, as by insertion through the opposite end of the tube 11, and will likewise enable the thru-bore 28 to be utilized for a manually operable plunger to be connected and/or removed therethrough.

Finger grip section 25 is formed in the illustrative and preferred embodiment as an integral flange having an enveloping annular portion including opposed extensions 25a and connecting side portions 25b. Other finger grip forms and constructions may be employed, including an annular flange having a constant diameter providing a round flange periphery, or the finger grip section may have integral molded finger gripping rings, or other suitable finger grip element or elements. However, the illustrative embodiment is preferred, and particularly in employing a fully annular enveloping flange portion extending laterally beyond the outer diameter of the sheath 23 and enabling the employing of annular fillet enlargement 27, particularly in the embodiments employing a fire-polished bead 17a on the end of the glass tube 11.

As previously stated, one or both of the end 17 of tube 11 and end 23a of sheath 23 is formed with a cam surface which effects a circumferential and diameter stretching action on the sheath 23 as a function of pressing of the sheath 23 axially against and onto the open end of glass tube 11. A cam surface on the end of finger grip sleeve sheath 23 may be formed as an annular bevel cam surface 23a, as shown, which may have an annular blunting beveled or flat surface formed at its radially outer edge, if desired, or which may be omitted if outer edge blunting is not desired. Alternatively, the surface 23a may be rounded or otherwise arcuately smoothly curved in whole or in part as viewed in longitudinal section, and as illustratively shown as applied to the nose-forming sleeve modification 231 in FIG. 7 as 233a, to provide the desired camming surface action with the end 17 of glass tube 11. Glass tube end 17 is preferably fire-polished to form a smooth radially outer end edge surface 17aa, which preferably forms a small bead of approximately 0.001–0.005 inch added diameter, and which bead will normally extend beyond the nominal cylindrical diameter of the tube 11 both radially outwardly and radially inwardly, as well as providing the desired convex arcuate outer can surface 17aa for camming interengagement with the interfacing end edge of sheath 23. (In this respect it will be appreciated that the drawings are largely schematic and that various parts or elements, such as bead 17a, have been exaggerated for purposes of illustration and clarity.) This small annular fire-polished bead serves a desired multiple purpose of cam stretching of the sheath as it is press-fit in enveloping interference fit over the end 17 and onto the longitudinal straight wall surface 12 of tube 11, as well as providing added retentive gripping effect and added strength to the glass tube at the end 17. The glass tube end 17 may alternatively be ground or otherwise formed with a beveled or rounded outer end edge surface corresponding to surface 17aa, which may enable effecting of the desired cam stretch fitting action on the sheath 23. Also alternatively, the sheath 23 may have its initially interfacing end edge blunt, without the highly desired dual camming provided by both level 23a and bead 17a, although it will be appreciated that a sharp outer annular edge surface on the tube 11 is not desirable in any event as such will ordinarily effect a scraping and material-removal action in attempting to insert the tube into the sheath 23, with consequent difficulty in assembly and reduction in retentive resistance of the sheath on the tube.

The fillet 27 forms an integral smoothly connecting annular corner between annular sheath 23 and annular finger grip flange secton 25. Fillet 27 serves also as an effectively elastic smoothly enlarged diameter reinforcement for the sheath 23 at the zone where the sheath 23 overlies the bead end 17a of tube 11. This smooth enlargement provided by the fillet 27 provides added strength and desirable lateral stress distribution in this zone, while enabling the sheath to adequately stretch in diameter and compress in thickness, without the cracking of glass tube 11 that might be caused by bottoming or terminating the glass tube end 17 in a zone within the grossly circumferentially enlarged and more rigid zone within the annular finger grip flange section 25, as well as enabling the material of the sleeve in the zone of fillet 27 to compensate for the added thickness of diameter of bead 17a and the expansion of sheath 23 necessary for the accommodation of the basic interference fit formed between the straight-walled section 13 of tube 11 with sheath 23 in this end overlie and flange grip connecting inner connection transition zone 27.

The invention has been applied in practical form to available glass tubing and employing thermoplastic resin sold by Rexall, the utilized theromplastic resin being a heat-stabilized grade marketed as Rexall PP-13S, 12 melt index. Glass tubing of a nominal cylindrical outer diameter along the cylindrical wall 13 of 0.414 inch, with a conventionally supplied tolerance range in diameter of approximately 0.034 inch, has been suitably utilized according to the preferred aspect of the invention. In this respect the thickness of sheath 23 may be suitably of the order of approximately 0.020–0.040 inch, and preferably in the range of 0.030–0.035 inch, the length of the sleeve sheath 23 being within the range of approximately 0.4' 0.7 inch in order to afford an adequate longitudinal extent of contiguous interfacing longitudinal wall seated interference retention fit between the sheath 23 and tube 11. The cylindrical inner wall 23c of sheath 23 may be very slightly tapered inwardly therealong from its open end adjacent annular beveled edge 23a, to the zone adjacent shoulder 29, as of the order of approximately 0.002 inch diameter change. The fillet enlargement nay have a radius of approximately 0.025–0.250 inch and preferably is in the range of approximately 0.100 inch for these sizes of sleeves and tubes. Glass tubes of the order of 0.020–0.040 inch, or greater, wall thickness may suitably be employed, using available commercial grades of glass, although tubing wall thickness of the order of as low as 0.010–0.015 inch may be utilized when employing high-strength glass for the glass tube 11. However, the smaller wall thicknesses are normally difficult to form and handle in other respects, and will not normally be desirable or necessary.

The indicated tolerance range which is available on a commercial basis from manufacturers of die-formed glass tubing, in the illustrative example of approximately 0.4 inch nominal outer diameter, namely approximately 0.034 inch tolerance, may be satisfactorily accommodated according to the invention by practicing the preferred mode of assembly of the tube 11 and sleeve 21, although the lower end of the tolerance range will not give as good pull-off resistance as the more desirable mid and upper portions of the tolernace range for a given sleeve size adapted to cover the total range of these tolerance variations, and sorting may be resorted to, if desired, to effectively increase the lower values of retentive resistance. In this preferred mode of assembly, the sleeve 21, which may be conventionally injection-molded, is first preheated prior to assembly to an elevated temperature and substantially above normal ambient room temperature, and the sleeve 21 is assembled with the glass tube 11 while the sleeve 21 is at such elevated temperature. It has been found suitable to heat the sleeves 21 to an elevated temperature of the order of approximately 100°–160° F, although it is believed that temperatures within a range of values slightly below and substantially above this temperature range may suitably be employed, dependent to an extent upon the tolerance limits which must be accommodataed in glass tubing sizes, it being appreciated that the upper temperature should not reach the tacky temperature zone for the theromplastic resin forming the sleeve 21. It has been found that by employing this preheating of the sleeve 21 and assembly of such with the glass tube 11 while in an elevated temperature condition, the range of interference tolerance which may be operably acceptable, between the internal diameter of the sheath 23 and its inner surface 23c and the normal outer wall diameter along the straight cylindrical wall section 13 of tube 11, may be substantially extended to accommodate commercial tolerance ranges of glass tubing, without requiring sorting. Thus, as noted, tolerance ranges of the order of approximately 0.034 inch for the outer diameter of glass tubing 11 of approximately 0.4 inch nominal outer diameter, may be accepted and used direct, without requiring sorting, while still providing adequate crack resistance of the thermoplastic resin sleeve 21, and without causing cracking of the glass tubing 11, either during, immediately after, or after long-term storage of, assembly 11, 21.

As noted heretofore, the nose-forming sleeve 31 is assembled onto glass tube 11 in the same manner and with essentially the same parameter criteria of entrance configurations, relative wall diameters, thicknesses, and longitudinal lengths of annular inner-wall engagement. In addition, in the illustrative embodiment, the sheath section 33 of nose-forming sleeve 31 has an extension section 33f which extends beyond the end 15 of glass tube 11, and may form a cavity 36 which is bonded on each end by tube end 15 and sleeve end wall 35. In this embodiment the sleeve 31 also has an annular sheath mid-section enlargement in the form of raised ring 33c which may serve a dual function of aiding in longitudinal positioning and force tansmitting press-on of the sleeve 31 by a female work holder 81 and of providing an annular reinforcement which is desirably positioned over or closely adjacent the zone of end 15 of glass tube 11. For a nose-forming sleeve 31 having an outer diameter of approximately 0.46 inch and an inner wall diamter of approximately 0.4 inch, with a forwardly decreasing diameter taper of approximately 0.001–0.004 inch along a total internal sheath wall length of approximately 0.76 inch, a ring enlargement of approximately 0.05 inch longitudinal width and approximately 0.51 inch outer diameter, with sheath extent 33b having a length of approximately 0.46 inch, has been found satisfactory for glass tubing of approximately 0.4 inch outer diameter, as previously discussed in relation to finger grip sleeve 21. Connector/dispenser tip 37 has a fluid discharge bore 39 formed therein, and may if desired by formed for suitable connection thereof to a needle unit, as by forming a Luer taper on tip 37, or a threaded connector surface, or other connection may be formed in sleeve 31 if and as may be desired. Also, while the illustrated nose-forming sleeve 31 is a preferred embodiment enabling various syringe combination constructions to be employed, including various tube seal arrangements, it will be appreciated that modifications may be made, as the instance the sheath extension 33f may be omitted and the end wall 35 may be bottomed against or brought closely adjacent tube end 15.

The invention may also be practiced by assembling the sleeves 21 and 31 onto the glass tube 11 while both the sleeves and the glass tube are at the normal ambient room temperatures; however, the maximum acceptable interference fit in this less desired mode of practice of the invention, as applied to standard glass tubing and polypropylene thermoplastic resin sleeves 21, 31, has been found to be approximately 0.030 inch, and the range of tolerances which may be accommodated in the outer diameter of the glass tubing is substantially reduced, and will be of the order of approximately 0.025–0.027 inch, as the lower limit acceptable interference fit is approximately 0.003–0.005 inch, as distinguished from the substantially wider interference fit tolerance range extending from a lower limit of approximately 0.003–0.005 inch to an upper limit of approximately 0.037–0.039 inch which has been found to be operable for the preferred heated sleeve mode of assembly as discussed above. In addition, in the less desired mode of practice in which sleeves 21 and 31 are assembled cold, substantial residual stresses do remain in the sleeves to an extent that such may, particularly after a long-term storage, result in cracking of the end sleeves along their respective sheaths: 23, 33, where the outer extent of the interference tolerance zone is approximately 0.030 inch is required or approached for a particular sorting utilization of glass tubing.

In a particular illustrative embodiment which utilizes glass tubing of nominal 0.414 inch outer diameter along the surface of the straight cylindrical wall section 13, and which was supplied within a specified commercial tolerance range of 0.401–0.435 inch, a polyproprylene thermoplastic resin finger grip sleeve 21 has been employed with a sheath inner diameter of aproximately 0.398 inch at its entrance end and approximately 0.396 inch adjacent shoulder 29, and a nose-forming sleeve 31 has been employed having a sheath inner diameter of approximataely 0.398 inch at its entrance end and approximately 0.396 inch adjacent end wall 35, utilizing the preferred preheated sleeve assembly method, it being noted that the resulting range of tolerances lies within the acceptable range of interference fit. The same nominal glass tube diameter of 0.414 inch may also be used in the less desired cold assembly method, with approximately the same inner wall diameters for the sheaths 23 and 33 by reducing the tolerance range of the glass tubing to within the acceptable tolerance of approximately 0.025–0.027 inch. In this illustrative embodiment, the sheath 23 has a total length of approximately 0.6 inch, and the fillet 27 has a radius of curvature of approximately 0.100 inch, with the finger grip flange section 25 having a longitudinal thickness of approximately 0.06 inch, and an outer flange extension diameter of approximately 0.9 inch. Also, in this illustrative embodiment the shoulder 29 has been formed with an inner thru-bore 28 diameter of approximately 0.314–0.317 inch. In further note of the zone 33b beyond the end 15 of tube 11, it has been found that there is a stress-related step-down of outer and inner sheath diameters directly beyond the tube end 15, the remaining extended extent of sheath 33 beyond end 15 being of approximately original molded or otherwise pre-assembly size, less any small extent of residual shrinkage effected by the heating operation during assembly.

Glass tube and polypropylene thermoplastic resin sleeve syringe body assemblies 10, constructed in accordance with the foregoing description have been found to provide sleeve pull-off resistance within the range of approximately 5 to 35 pounds, when the glass tube 11 is in a clean condition without lubricant such as silicone thereon. When the glass tube 11 has silicone coating thereon, as may sometimes be desirable for other operational conditions such as the subsequent insertion of a plunger piston or slidable plug in the glass tube, the retentive resistance formed by the interference fit between the sleeves 21 and 31 and the glass tube 11 has been found to be reduced by the order of approximately 20 percent, and accordingly the lower range of interference tolerances may not be acceptable for a given required use where the retentive force required for utilization of the assembly in a given instance may be greater than the retentive resistance afforded by this lower range of tolerance fit. Such deficiency may be overcome by sorting, or otherwise insuring that the interference fit is sufficient to provide the desired retentive resistance to pull-off of the sleeve 21 and 31 from the glass tube 11. A modified form of practice of the invention is illustrated in FIGS. 4 and 5, in which the glass tube 11 has raised spaced protrusions 13a on its surface, as may be provided by printing of graduations, legends, etc. on the glass tube 11 prior to assembly with the sleeves 21 and 31. This printing may be formed as by application of epoxy ink which is subsequently cured in situ on the glass tube or by the application of ceramic ink subsequently fired in place on the glass tube, the utilization of such inks to form graduations and other indicia being commonly and readily understood in the art, and such will accordingly not be further described herein, other than to note that such may suitably provide a raised added wall thickness and enlargement of the order of approximately 0.001–0.002 inch. As will be noted from FIGS. 4 and 5, these raised surface segments 13a lie beneath one or both of the sleeves 21 and 31, and afford additional retentive resistance to the removal of the sleeves in the course of usage of the syringe body assembly 10. While depressions may also be formed in the glass tube outer wall surface, for added retentive resistance, untempered scoring to form such depressions is not desirable as the glass is subseequently weakened along such score lines, which may result in subsequent cracking during or after assembly.

Simultaneous assembly of the finger grip sleeve 21 and nose-forming sleeve 31 onto the glass tube 11 is illustrated in FIG. 8, in which a work holder 71 having a gripping nipple 73 with a tapered nose 73a and cylindrical gripping surface 73a engages in releasable frictional holding relation with the bore-forming surface of the shoulder 29, on sleeve 21, a female work holder 81 engaging in releasable frictional holding relation with the nose-forming sleeve 31 and abutting against ring 33c of sheath 33 and in which glass tube 11 is held in a suitably formed guide chuck 61 which may be a V-chuck, with the glass tube either vertical or horizontal.

The work holders 71, 81 are moved toward the respective opposite ends 17, 15 of glass tube 11 to move the sleeve sheaths 23 and 33 into end contact with and into interference gripping relationship about respectively relatively long extends of the glass tube 11, the force required for this being transmitted through the forward face 75 of work holder 71 and the forward face and internal holding cavity of work holder 81. After completion of assembly, the syringe body assembly 11, 21, 31 may be removed from the chuck 61, and the entire procedure may be repeated with a succeeding glass tube and finger grip and nose-forming sleeves. Alternatively each sleeve 21 and 31 may be assembled onto glass tube 11 separately, if so desired.

While the invention has been illustrated and described with respect to various preferred and other embodiments and modes of practice thereof, it will be appreciated that various modifications may be made without departing from the scope and spirit of the invention. Accordingly, the invention is not to be limited by the illustrative embodiment but only by the scope of the appended claims.

I claim:

1. A glass tube and non-glass finger-grip and nose-forming arrangement for use particularly in packaging and subsequent dispensing of chemicals, comprising:
   a substantially cylindrical glass tube formed of a length of substantially constant diameter thin-walled glass tubing of substantially constant wall thickness along its length and having a wall thickness substantially smaller than the outer and inner wall diameters of said glass tubing,
   a finger-grip sleeve of thermoplastic resin and having a tube-gripping sheath section with laterally extending finger-grip protrusions integrally formed thereon,
   and a nose-forming sleeve of thermoplastic resin and having a reduced diameter section integral with a tube-gripping sheath section thereof,
   said sleeves being frictionally secured in annularly extending stretch-fit along their sheath sections over and along respectively opposite ends of said glass tube,
   a sloped annular cam surface formed on one of the longitudinally inner end of said sheath section of said finger-grip sleeve and the respective longitudinally outer said end of said glass tube,
   and a sloped annular cam surface formed on one of the longitudinally inner end of said sheath section of said nose-forming sleeve and the respective said end of said glass tube,
   at least one of said slope annular cam surfaces being formed on said one end of said glass tube,
   at least one of said sloped annular cam surfaces being smoothly arcuate in longitudinal section,
   at least one of said sloped annular can surfaces being formed by and as a part of an annular fire-polished rim formed on one end of said glass tube,
   said annular fire-polished rim comprising a fire-polished raised annular bead, and said fire-polished bead being formed at both longitudinal ends of said glass tube,
   both of said sleeves sheaths having a laterally outwardly extending annular enlargement section at and in substantial lateral encompassing relation with the respective annular fire-polished end bead on said glass tube,
   said finger-grip sheath annular enlargement being a fillet connecting with an annular finger-grip section, and
   said annular enlargement on said nose forming sleeve forming a raised ring disposed in spaced relation from the opposite longitudinal ends of its respective said sheath section.

2. A glass tube and non-glass finger-grip and nose-forming arrangement for use particularly in packaging and subsequent dispensing of chemicals, comprising:
   a substantially cylindrical glass tube formed of a length of substantially constant diameter thin-walled glass tubing of substantially constant wall thickness along its length and having a wall thickness substantially smaller than the outer and inner wall diameters of said glass tubing,
   a finger-grip sleeve of thermoplastic resin and having a tube-gripping sheath section with laterally extending finger-grip protrusions integrally formed thereon,
   and a nose-forming sleeve of thermoplastic resin and having a reduced diameter section integral with a tube-gripping sheath section thereof,
   said sleeves being frictionally secured in annularly extending stretch-fit along their sheath sections over and along respectively opposite ends of said glass tube,
   a sloped annular can surface formed on one of the longitudinally inner end of said sheath section of said finger-grip sleeve and the respective longitudinally outer said end of said glass tube,
   and a sloped annular cam surface formed on one of the longitudinally inner end of said sheath section of said nose-forming sleeve and the respective said end of said glass tube,
   at least one of said sloped annular cam surfaces being formed on said one end of said glass tube,
   at least one of said sloped annular cam surfaces being smoothly arcuate in longitudinal section,
   at least one of said sloped annular can surfaces being formed by and as part of an annular fire-polished rim formed on one end of said glass tube,
   said annular fire-polished rim comprising a fire-polished raised annular bead, and said fire-polished bead being formed at both longitudinal ends of said glass tube, and
   said nose-forming sleeve having a raised annular engagement ring section at and in substantial encompassing relation with said one annular fire-polished and bead on said glass tube, said ring being disposed in spaced relation from the opposite longitudinal ends of the sheath section of said nose-forming sleeve.

* * * * *